United States Patent
Czech et al.

(10) Patent No.: US 7,851,581 B2
(45) Date of Patent: Dec. 14, 2010

(54) FILM FORMING COMPOSITION WITH SPREADING PROPERTIES

(75) Inventors: Anna M. Czech, Bronxville, NY (US); Benjamin Falk, Yorktown Heights, NY (US); John Nicholson, Ramsey, NJ (US); George A. Policello, Ossining, NY (US); Jo Anne Tully, Mahopac, NY (US)

(73) Assignee: Momentive Performance Materials Inc., Albany, NY (US)

( * ) Notice: Subject to any disclaimer, the term of this patent is extended or adjusted under 35 U.S.C. 154(b) by 239 days.

(21) Appl. No.: 11/840,304

(22) Filed: Aug. 17, 2007

(65) Prior Publication Data

US 2008/0107696 A1    May 8, 2008

Related U.S. Application Data

(60) Provisional application No. 60/823,105, filed on Aug. 22, 2006.

(51) Int. Cl.
*C08G 77/60* (2006.01)
(52) U.S. Cl. .......................... 528/35; 428/405
(58) Field of Classification Search ............ 528/35; 428/405
See application file for complete search history.

(56) References Cited

U.S. PATENT DOCUMENTS

| | | | |
|---|---|---|---|
| 4,902,499 | A | 2/1990 | Bolish, Jr. |
| 5,188,899 | A | 2/1993 | Matsumoto et al. |
| 6,589,519 | B1 | 7/2003 | Restle et al. |
| 6,696,051 | B2 | 2/2004 | Barbuzzi et al. |
| 2004/0131570 | A1 | 7/2004 | Suenaga et al. |
| 2004/0197286 | A1 | 10/2004 | Robert et al. |

FOREIGN PATENT DOCUMENTS

| | | |
|---|---|---|
| EP | 0791384 | 8/1997 |
| EP | 1287808 | 3/2003 |
| EP | 1380282 | 1/2004 |
| EP | 1702974 | 9/2006 |
| JP | 10114622 | 5/1998 |
| WO | 02/087522 | 7/2002 |
| WO | 02/085316 | 10/2002 |

*Primary Examiner*—Kuo-Liang Peng
(74) *Attorney, Agent, or Firm*—Kenneth S. Wheelock

(57) ABSTRACT

A film forming composition with spreading properties derived from an aqueous emulsion comprising (I) colloidal silica core/silicone shell particles consisting of (a) 90 wt % to 10 wt % cores of colloidal silica and (b) 10 wt % to 90 wt % shells of polyorganosiloxane; (II) a polyalkyleneoxide modified trisiloxane; (III) an emulsifier package consisting of at least one anionic surfactant, and (IV) the salt of an acidic polymerization catalyst. The composition may include optional ingredients useful in Personal Care, Hair Care, Skin Care, Agricultural, and Home Care applications.

19 Claims, No Drawings

FILM FORMING COMPOSITION WITH SPREADING PROPERTIES

CROSS-REFERENCE TO RELATED APPLICATIONS

This application claims priority claims priority to U.S. provisional patent application 60/823,105 filed Aug. 22, 2006.

FIELD OF THE INVENTION

The present invention relates to a film forming composition useful in hair styling, agricultural and home care applications where the composition of the present invention contains colloidal silica core/silicone shell particles and polyalkyleneoxide modified trisiloxane, and more particularly, to a hair styling composition giving satisfactory setting retention and smooth feeling with no "tack time".

BACKGROUND OF THE INVENTION

A hair styling composition generally contains a high-molecular compound in order to impart hair setting retention. Specifically, a high-molecular compound such as a polyvinylpyrrolidone-based high-molecular compound, a polyvinylether-based high-molecular compound, a polyvinyl acetate-based high-molecular compound is used therein, or an acryl-based high-molecular compound. The blend of such a high-molecular compounds, however, cannot be fully satisfactory in terms of smooth feeling and drying properties (they go through a very unpleasant "tack time" period), though it is capable of imparting high setting retention.

Various patent documents disclose that the use of silicone is advantageous in giving smoothness to hair. However, there exists a problem, that excessive use of silicone extremely softens hair to impair setting retention and, deprives hair, especially when they are thin, of firmness to make it difficult to handle.

Further, the specification of U.S. Pat. No. 4,902,499 discloses a hair styling composition comprising a specific silicone polymer dissolved in a volatile carrier in order to increase hair setting retention. This hair care cosmetic composition is prepared in such a manner that silicone gum, silica or silicone elastomer, and a silicone resin are dissolved in a volatile carrier such as octamethyltetrasiloxane, and the resultant composition is useful for hair cosmetics. Further, the specification of Japanese Patent No. 3043816 discloses a hair care cosmetic composition which gives setting retention and smoothness to hair by the use of cross-linked silicone. Further, Japanese Patent Laid-open No. Hei 10-114622 discloses the use of silica core/silicone shell particles for hair cosmetics. It is noted that the invention disclosed in this laid-opened publication comprises silica core/silicone shell particles independently and in No. Hei 10-114622 any effect obtained when polyalkyleneoxide modified trisiloxane is blended therein is not described.

As mentioned above, the use of specific silicone as hair care cosmetics has been already known, but any of hair care cosmetics obtained by these well-known arts is not fully satisfactory in terms of hair setting retention and feeling such as smoothness and aesthetics upon drying, and further improvement has been desired.

The present invention is made from such viewpoints. It is an object of the present invention to provide a hair styling composition, which does not satisfactory setting retention and smooth feel but also overcomes the "tack time".

SUMMARY OF THE INVENTION

The present invention provides for a composition comprising:

a) Colloidal silica core/silicone shell particles comprising (i) about 90 wt % to about 10 wt % cores of colloidal silica and (ii) about 10 wt % to about 90 wt % shells of a polyorganosiloxane having the formula $$M_a D_b T_c Q_d$$

with
$M_a = (R^1)(R^2)(R^3)SiO_{2/2}$
$D_b = (R^4)(R^5)SiO_{2/2}$,
$T_c = (R^6)SiO_{3/2}$,
$Q_d$ selected from the group consisting of (OH) $SiO_{3/2}$ or $SiO_{4/2}$ where $R^1$, $R^2$, $R^3$, $R^4$, $R^5$, and $R^6$ are each independently selected from the group consisting of OH, linear or branched monovalent hydrocarbon radicals of 1 to 30 carbons, monovalent arylalkyl, aryl cyclics hydrocarbon radicals where the ratios of M to D to T to Q are according to the following relationships:

$$0 < (a/d) < 2;$$

$$0.1 < (b/d) < 10;$$

$$0 < (c/d) < 10;$$

b) a polyalkyleneoxide modified trisiloxane having the formula:

$$M^1_e D^1_f D^2_g M^2_h$$

with
$M^1_e = R^7 R^8 R^9 SiO_{1/2}$;
$M^2_h = R^{10} R^{11} R^{12} SiO_{1/2}$;
$D^1_f = R^{13} R^{14} SiO_{2/2}$;
$D^2_g = R^{15} R^{16} SiO_{2/2}$;

where $R^7$, $R^{10}$ and $R^{15}$ are each independently selected from the group consisting of or 1 to 4 monovalent hydrocarbon radicals or $R^{17}$;

subject to the following relationship that when g=0 then $R^7$ and $R^{10}$ are both $R^{17}$ when g is non-zero $R^7$ and $R^{10}$ are each independently selected from the group consisting of 1 to 4 monovalent hydrocarbon radicals;

$R^{15}$ is $R^{17}$;

$R^8$, $R^9$, $R^{11}$, $R^{12}$, $R^{13}$, $R^{14}$ and $R^{16}$ are independently selected from a group consisting of 1 to 4 monovalent hydrocarbon radicals;

where the subscripts e, f, g and h are zero or 1 subject to the following relationship:

$$e+f+g+h=3;$$

with the requirement that when g is 0, then $R^7$ or $R^{10}$ are $R^{17}$;
$R^{17}$ is an alkylenoxide group having the formula:

$$R^{18}O(C_2H_4O)_j(C_3H_6O)_k(C_4H_8O)_m R^{19}$$

where $R^{18}$ is a linear or branched hydrocarbon radical having from 2 to 6 carbons, $R^{19}$ is selected from the group consisting of H, acetyl or a monovalent hydrocarbon radical of 1 to 6 carbon atoms and the subscripts j, k, and m are zero or a positive integer subject to the limitation that $4 < j+k+m \leq 20$;

c) an emulsifier comprising an anionic surfactant derived selected from the group consisting of alkylarylsulfonates, alkylsulfonates, alkylsulfates and alkylethersufates, alkyl phosphate esters, alkylaryl phosphate esters, alcoholalkoxylate phosphate esters, and alkylarylalkoxylate phosphate esters and mixtures thereof, and d) the salt of an acidic polymerization catalyst.

The compositions of the present invention are useful in forming films

DETAILED DESCRIPTION OF THE INVENTION

It has been found that that the blend of silica core/silicone shell particles, in which colloidal silica and polyorganosiloxane are siloxane-bonded together, and polyalkyleneoxide modified trisiloxane in hair cosmetics at a specific weight ratio not only imparts satisfactory setting retention to the hair cosmetics and smooth feel, but also unexpectedly eliminates "tack time".

A film forming composition with spreading properties derived from an aqueous emulsion comprising (I) colloidal silica core/silicone shell particles consisting of (1) 90 wt % to 10 wt % cores of colloidal silica and (2) 10 wt % to 90 wt % shells of polyorganosiloxane represented by the mean formula $$M_a D_b T_c Q_d$$

where
$M_a$ is $(R^1)(R^2)(R^3)SiO_{2/2}$
$D_b$ is $(R^4)(R^5)SiO_{2/2}$,
$T_c$ is $(R^6)SiO_{3/2}$,
$Q_d$ is $(OH)SiO_{3/2}$, or $SiO_{4/2}$ where $R^1$, $R^2$, $R^3$, $R^4$, $R^5$, and $R^6$ is selected from the group consisting of OH, linear or branched monovalent hydrocarbon radical of 1 to 30 carbons, arylalkyl, aryl, and hydrocarbon cyclics, each of which may be unsubstituted or optionally substituted with heteroatoms such as fluorine, nitrogen, oxygen and sulfur.

where the ratios of M to D to T to Q is according to the following relationships:

$$0<(a/d)<2$$

$$0.1<(b/d)<10$$

$$0<(c/d)<10$$

(II) polyalkyleneoxide modified trisiloxane, or a hydrolytically stable silicon based surfactant. and (III) an emulsifier package consisting of at least one anionic surfactant derived from alkylarylsulfonates, alkylsulfonates, alkylsulfates and alkylethersufates, alkyl phosphate esters, alkylaryl phosphate esters, alcoholalkoxylate phosphate esters, and alkylarylalkoxylate phosphate esters.

and (IV) the salt of an acidic polymerization catalyst.

Component I is present at a concentration between 0.1 wt. % and 40 wt. %; Component II is present at a concentration between 0.1 wt. % and 20 wt. %; Component III is present at a concentration between 0.25 wt. % and 10 wt. %.

Component IV is present at a concentration between 0.1 wt. % to 5 wt. %.

Optional ingredients selected from organosilicone polyether copolymers, solvents and fragrances.

According to the present invention, the use of colloidal silica core/silicone shell particles and polyalkyleneoxide modified trisiloxane together can not only give high setting retention, smoothness and combing easiness but also no tacky feel during drying. Additionally the composition of the present invention, when applied to foliar surfaces, provides a water repellant characteristic. Additionally the composition of the present invention gives selective wetting, causing the spray droplets to not to initially adhere to leaf surfaces thereby delivering said spray below the foliar canopy allowing the agrochemical spray to wet the soil.

A film forming composition comprising (I) colloidal silica core/silicone shell particles as described in the specification of Japanese Patent No. 2992591 consisting of (1) 90 wt % to 10 wt % cores of colloidal silica and (2) 10 wt % to 90 wt % shells of polyorganosiloxane represented by the formula $$M_a D_b T_c Q_d$$

where
$M_a$ is $(R^1)(R^2)(R^3)SiO_{2/2}$
$D_b$ is $(R^4)(R^5)SiO_{2/2}$,
$T_c$ is $(R^6)SiO_{3/2}$,
$Q_d$ is $(OH)SiO_{3/2}$, or $SiO_{4/2}$ where $R^1$, $R^2$, $R^3$, $R^4$, $R^5$, and $R^6$ is selected from the group consisting of OH, linear or branched monovalent hydrocarbon radical of 1 to 30 carbons, arylalkyl, aryl, and hydrocarbon cyclics, each of which may be unsubstituted or optionally substituted with heteroatoms such as fluorine, nitrogen, oxygen and sulfur.

where the ratios of M to D to T to Q is according to the following relationships:

$$0<(a/d)<2$$

$$0.1<(b/d)<10$$

$$0<(c/d)<10$$

(II) a polyalkyleneoxide modified trisiloxane of the general formula:

$$M^1_e D^1_f D^2_g M^2_h$$

$M^1_e = R^7 R^8 R^9 SiO_{1/2}$;
$M^2_h = R^{10} R^{11} R^{12} SiO_{1/2}$;
$D^1_f = R^{13} R^{14} SiO_{2/2}$;
$D^2_g = R^{15} R^{16} SiO_{2/2}$;

wherein $R^7$, $R^{10}$ and $R^{15}$ are independently selected from $R^{17}$ or independently selected from a group consisting of 1 to 4 monovalent hydrocarbon radicals;

and subject to the following relationship:

when g=0 then $R^7$ and $R^{10}=R^{17}$ otherwise independently selected from a group consisting of 1 to 4 monovalent hydrocarbon radicals;

$R^{15}$ is $R^{17}$; $R^8$, $R^9$, $R^{11}$, $R^{12}$, $R^{13}$, $R^{14}$ and $R^{16}$ are independently selected from a group consisting of 1 to 4 monovalent hydrocarbon radicals;

where the subscripts e, f, g and h are zero or 1 subject to the following relationship:

$$e+f+g+h=3;$$

with the requirement that when g is 0, then $R^7$ or $R^{10}$ are $R^{17}$; $R^{17}$ is an alkylenoxide group of the general structure:

$$R^{18}O(C_2H_4O)_j(C_3H_6O)_k(C_4H_8O)_m R^{19}$$

where $R^{18}$ is a linear or branched hydrocarbon radical having 2 to 6 carbons. $R^{19}$ is selected from the group consisting of H, acetyl or a monovalent hydrocarbon radical of 1 to 6 carbon atoms j, k, and m are zero or a positive integer and subject to the relationship: $4<j+k+m \leq 20$ One embodiment of the polyalkyleneoxide modified trisiloxane is where $R^7, R^8, R^9, R^{10}, R^{11}, R^{12}$ are methyl, j is 5 to 6, k is 2 to 3, m is 0, and $R^{18}$ is 3 to 4, $R^{19}$ is methyl or hydrogen.

Non-limiting illustrative examples of $R^{17}$ are:

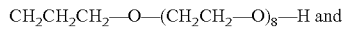

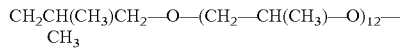

and (III) an emulsifier package comprising an anionic surfactant derived selected from the group consisting of from alkylarylsulfonates, alkylsulfonates, alkylsulfates and alkylethersufates, alkyl phosphate esters, alkylaryl phosphate esters, alcoholalkoxylate phosphate esters, and alkylarylalkoxylate phosphate esters.

and (IV) the salt of an acidic polymerization catalyst.

Component I is present at a concentration between 0.1 wt. % and 40 wt. %; Component II is present at a concentration between 0.1 wt. % and 20 wt. %; Component III is present at a concentration between 0.25 wt. % and 10 wt. %.

Component IV is present at a concentration between 0.1 wt. % to 5 wt. %.

Optional ingredients may be selected from organosilicone polyether copolymers, solvents and fragrances Specific examples of optional ingredients useful in the present invention include, but not limited too, fragrance components, Polyurethane-1, Polyurethane-6, Acrylates Copolymer, Acrylates/C1-2 Succinates/HydroxyAcrylates Copolymer, Isobutylene/Ethylmaleimide/Hydroxyethylmaleimide Copolymer, Polyimide-1, Polyvinylpyrrolidone Vinylacetate, Polyurethane-14 (and) AMP-Acrylates Copolymer, Polyquatemium-55, Polyquatemium-68, Polyquatemium-72, Silicone Quaternium-16/Glycidoxy Dimethicone Crosspolymer and Trideceth-12, Modified Corn Starch, Octylacrylamide/Acrylates/Butylaminoethyl/methacrylate Copolymer, VA/Crotonates/Vinyl Neodecanoate Copolymer, Ethyl Ester of PVM/MA Copolymer, Acrylates/Hydroxyesters Acryloates Copolymer, Aminomethyl propanol, Chitosan PCA, Polyvinylpyrrolidone, Hydrolyzed Wheat Starch.

These fragrance components may be fragrance compounds, encapsulated fragrance compounds, or fragrance releasing compounds that either the neat compounds or are encapsulated. Particularly compatible with the compositions of the present invention are the fragrance releasing silicon containing compounds as disclosed in U.S. Pat. Nos. 6,046,156; 6,054,547; 6,075,111; 6,077,923; 6,083,901; and 6,153,578; all of which are herein and herewith specifically incorporated by reference.

A suitable group of silicone additives can be selected from the class of $AB_n$ copolymers formed by the hydrosilation of hydride terminated polydimethylsiloxane and an olefinically modified polyalkyleneoxide, such as allyl or methallyl terminated polyalkyleneoxides. Additives of this type follow the general structure:

where $A^1$ has the general structure:

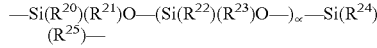

and $B^1$ has the general structure:

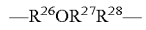

where $R^{20}, R^{21}, R^{22}, R^{23}, R^{24}$ and $R^{25}$ are independently selected from a monovalent hydrocarbon radical of 1 to 4 carbons; t is 2 to 20; $\alpha$ is 0 to 50; $R^{26}$ and $R^{28}$ are independently selected from a divalent hydrocarbon radical of 2 to 10 carbons $Y^1$ or $Y^2$; $Y^1$ and $Y^2$ are independently selected from a monovalent hydrocarbon radical of 1 to 6 carbons, each optionally OH substituted, or $R^{29}$, where $R^{29}$ is $CH_2=CH(R^{30})(R^{31})_p-$; $R^{30}$ is H or methyl; $R^{31}$ is selected from a divalent hydrocarbon radical of 1 to 7 carbons; p is 0 or 1, and the subscript n ranges from about 2 to about 1000; specifically from about 3 to about 800; more specifically from about 5 to 600; and most specifically from about 5 to 500. It is noted that the foregoing structure for $Y^1(A^1B^1)_nY^2$ is empirical and thus subtends geometric and structural and isomers, e.g. block and random copolymers.

$R^{27}$ is selected from a group of polyalkyleneoxide radicals of the following structure:

$-(C_2H_4O)_q(C_3H_6O)_r(C_4H_8O)_s-$, where subscripts q+r+s are zero or positive and satisfy the following relationships: $2 \leq q+r+s \leq 100$.

The polyalkyleneoxide radical may also be blocked or random.

Additional suitable silicone additives may be selected from the class of amino modified Non-$(AB)n$ and random block structures formed by the ring opening of an epoxide, with an amine-connecting group. Silicone additives of this nature are represented by $(A^2B^2C^1)_t$ where $A^2$ has the general structure:

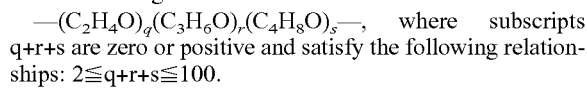

$B^2$ is an amine-connecting group with the general formula:

$C^1$ is a polyalkyleneoxide moiety of the general structure:

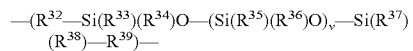

where $R^{33}, R^{34}, R^{35}, R^{36}, R^{37}$ and $R^{40}$ are independently selected from a monovalent hydrocarbon radical of 1 to 4 carbons; t is 2 to 1000; v is 0 to 50; $R^{32}$ and $R^{39}$ are independently selected from a divalent hydrocarbon radical of 2 to 10 carbons, which are optionally OH substituted, or $R^{45}$; $R^{45}$ is an epoxy group of the general formula:

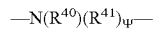

where $R^{46}$ and $R^{47}$ are independently selected from a divalent hydrocarbon radical of 1 to 10 carbons; $R^{48}$ is $-CH(O)CH_2$, or a cyclohexeneoxide of the formula $-C_6(R^{49})_uH_{9-u}O$; $R^{49}$ is a monovalent hydrocarbon group of 1 to 2 carbon atoms; $R^{41}$ is hydrogen, a monovalent hydrocarbon radical of 1 to 4 carbons, and a hydrocarbon radical containing an OH group; subscripts L and I are 0 or 1; u is 0 to 2; $\Psi$ is 0 or 1 and the subscript t ranges from about 2 to about 1000; specifically from about 3 to about 800; more specifically from about 5 to 600; and most specifically from about 5 to 500. It is noted that the foregoing structure for $(A^2B^2C^1)_t$ is empirical and thus subtends geometric and structural and isomers, e.g. block and random copolymers.

$R^{42}$ and $R^{44}$ are independently selected from a divalent hydrocarbon radical of 2 to 10 carbons, which are optionally OH substituted, or $R^{50}$; $R^{43}$ is selected from a group of polyalkyleneoxide radicals of the following structure:

$-(C_2H_4O)_\sigma(C_3H_6O)_e(C_4H_8O)_z-$, where subscripts $\sigma+e+z$ are zero or positive and satisfy the following relationships: $2 \leq \sigma+e+z \leq 100$.

The polyalkyleneoxide radical may also be blocked or random.

$R^{50}$ is an epoxy group of the general formula:

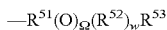

$$-R^{51}(O)_\Omega(R^{52})_w R^{53}$$

where $R^{51}$ and $R^{52}$ are independently selected from a divalent hydrocarbon radical of 2 to 10 carbons; $R^{53}$ is —CH(O)CH$_2$, or a cyclohexeneoxide of the formula —C$_6$(R$^{54}$)$_\Psi$H$_{9-\Psi}$O.

$R^{54}$ is a monovalent hydrocarbon group of 1 to 2 carbon atoms. Subscripts $\Omega$ and w are 0 or 1; $\Psi$ is 0 to 2.

The arrangement of $A^2$, $B^2$ and $C^1$ may be blocked or random.

The colloidal silica core/silicone shell particles used by the present invention may take several forms, where none, some or all of the silanol groups of the polyorganosiloxane component condense with the surface silanol groups of the silica by siloxane bonding.

The component (1) colloidal silica of the colloidal silica core/silicone shell particles is aqueous dispersed particles with SiO$_2$ being a basic unit and the average particle diameter thereof is 4 nm to 300 nm, more preferably, 20 nm to 150 nm.

Colloidal silica exists both acidic and basic forms in terms of property classification, and either of them is usable by appropriate selection depending on conditions of emulsion polymerization in producing the core-shell particles. For example, the use of acid colloidal silica is preferable for emulsion polymerization under acid conditions using an anionic surfactant.

The weight ratio of the component (2) of the colloidal silica core/silicone shell particles, namely, the shells of polyorganosiloxane according to the present invention is selected within a range of 10 wt % to 90 wt %. The reason is that polyorganosiloxane, when it is less than 10 wt %, cannot fully cover the surface of colloidal silica, resulting in colloidal silica core/silicone shell particles inferior in stability, and polyorganosiloxane, when it is more than 90 wt %, does not produce a sufficient reinforcing property of colloidal silica, resulting in elastomeric cured material lacking mechanical properties. In short, any weight ratio falling outside the aforesaid range does not result in a hair styling composition which gives setting retention.

Specific examples of the unsubstituted monovalent hydrocarbon group are a straight-chain or branched-chain alkyl group such as methyl, ethyl, propyl, hexyl, octyl, decyl, hexadecyl, and octadecyl; an aryl group such as phenyl, naphthyl, and xenyl; an aralkyl group such as benzyl, β-phenylethyl, methylbenzyl, and a naphthylmethyl group; a cycloalkyl group such as cyclohexyl and cyclopentyl; and so on.

Specific examples of the substituted monovalent hydrocarbon group are generally 3,3,3-trifluoropropyl, 3-fluoropropyl, and so on, each of which is a group in which a carbon or hydrogen atom of the aforesaid unsubstituted monovalent hydrocarbon group is substituted by a fluorine, nitrogen, oxygen, and sulfur.

The hair styling composition according to the present invention can be generally manufactured in the following procedure. Specifically, prepared are (1) colloidal silica (core component) and (2) organosiloxane which has a structural unit represented by $(R^{55})(R^{56})SiO_{2/2}$ (where $R^{55}$ and $R^{56}$ are a substituted or unsubstituted monovalent hydrocarbon group and which contains no hydroxyl group, the number of silicon atoms thereof being 3 to 7). Next, the organosiloxane is condensation polymerized with colloidal silica in a water medium in the presence of a surfactant so that an emulsion of the colloidal silica core/silicone shell particles is prepared.

In preparing the above-mentioned emulsion of the colloidal silica core/silicone shell particles, require the presence of an anionic surfactant to achieve the desired level of emulsion stability. An amount of water in this emulsification is 30 wt. % to 99.55 wt. %, preferably, 30 wt. % to 90 wt. %, more preferably 30 wt. % to 80 wt. %. Component I is present at a concentration between 0.1 wt. % and 40 wt. %, preferably, 5 wt. % to 30 wt. %, more preferably 10 wt. % to 30 wt. %; Component II is present at a concentration between 0.1 wt. % and 20 wt. %, preferably 0.25 wt. % to 10 wt. %, more preferably 0.5 wt. % to 5 wt. %; Component III is present at a concentration between 0.25 wt. % and 10 wt. %, preferably 0.25 wt. % to 5 wt. %; Component IV is present at a concentration between 0.1 wt. % to 5 wt. %, preferably between 0.25 wt. % and 3.5 wt. %.

Additionally, the above emulsion may be diluted in personal care, agricultural and textile formulations to a use level between 0.1 wt. % and 50 wt. %.

Further, the temperature in the process (condensation reaction and so on) of preparing the colloidal silica core/silicone shell particles is about 5° C. to about 100° C. Incidentally, in the organosiloxane component constituting the silicone shells, a cross-linking agent such as silane having a functional group may be added in order to increase the strength of the shell.

Since the emulsion of the colloidal silica core/silicone shell particles exhibits an acid property or an alkaline property, it is neutralized by the addition of alkali or acid in order to maintain long-term stability. Examples used here as an alkaline neutralizing agent are sodium hydroxide, thorium carbonate, thorium hydrogen carbonate, triethanolamine, and so on, and examples of an acid neutralizing agent are hydrochloric acid, sulfuric acid, nitric acid, acetic acid, phosphoric acid, glycolic acid, oxalic acid, and so on.

The following are specific examples of the aforesaid polyorganosiloxane that is a source component of polyorganosiloxane forming the shells of the core/shell particles used in the present invention.

They are cyclic compounds such as hexamethylcyclotrisiloxane, octamethylcyclotetrasiloxane, decamethylcyclopentasiloxane, 1,3,5,7-tetramethyl-1,3,5,7-tetraphenylcyclotetrasiloxane, 1,3,5,7-tetrabenzyltetramethylcyclotetrasiloxane, and 1,3,5,7-tris-(3,3,3-trifluoroprophyl) trimethylcyclotetrasiloxane, and one of them or a mixture of two kinds or more thereof may be used.

As a silane compound used for introducing a group including an organic functional group, the following silanes are used.

Specific examples of the silane compound including the organic functional group are 3-aminopropylmethyldimethoxysilane, 3-aminopropyltrimethoxysilane, N-(2-aminoethyl)-3-aminopropyltrimethoxysilane, N-triethylenediaminepropylmethyldimethoxysilane, 3-glycidoxypropylmethyldimethoxysilane, 3,4-epoxycyclohexylethyltrimethoxysilane, 3-mercaptopropyltrimethoxysilane, trifluoropropyltrimethoxysilane, 3-carboxypropylmethyldimethoxysilane, and so on, and one of them or a mixture of two kinds or more thereof may be used.

An anionic surfactant or a cationic surfactant is appropriately used as the surfactant mainly playing an emulsifying function in preparing the emulsion of the colloidal silica core/silicone shell particles according to the present invention.

As the anionic surfactant used here, aliphatic substituted benzenesulfonic acid, aliphatic hydrogen sulfate, a mixture of unsaturated aliphatic sulfonic acid and hydroxylated aliphatic sulfonic acid are preferable, which are represented by the following general formulas respectively.

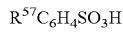

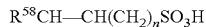

Note that in the formulas, $R^{57}$ is a monovalent aliphatic hydrocarbon group with the number of its carbon atoms being 6 to 30 (preferably 6 to 18), $R^{58}$ is a monovalent aliphatic hydrocarbon group with the number of its carbon atoms being 1 to 30 (preferably 6 to 18), and w is such an integer that the total number of carbon atoms becomes 6 to 30.

Specific examples of $R^{57}$ and $R^{58}$ are a hexyl group, an octyl group, a decyl group, a dodecyl group, a cetyl group, a stearyl group, a myricyl group, an oleyl group, a nonenyl group, an octynil group, a phytyl group, a pentadecadienyl group, and so on. Specific examples of the anionic surfactant having the $R^{58}$ group are hexylbenzene sulfonic acid, octylbenzene sulfonic acid, dodecylbenzene sulfonic acid, cetylbenzene sulfonic acid, octylsulfate, laurylsulfate, oleylsulfate, cetylsulfate, and so on. Examples of the anionic surfactant having the $R^{57}$ group are tetradecene sulfonic acid, hydroxytetradecane sulfonic acid, and so on.

Additionally, anionic surfactant weak in catalysis, for example, sodium salt, ammonium salt, and triethanolamine salt among the anionic surfactants represented by the above general formulas are usable when they are used along with a polymerization catalyst, examples of such surfactants being sodium dodecylbenzenesulfonate, sodium octylbenzenesulfonate, ammonium dodecylbenzenesulfonate, sodium laurylsulfate, ammonium laurylsulfate, triethanolamine laurylsulfate, sodium tetradecenesulfonate, sodium hydroxytetradecenesulfonate, and so on.

The polymerization catalyst used is generally a catalyst used in polymerization of low molecular weight organosiloxane, for example, aliphatic substituted benzenesulfonic acid, aliphatic hydrogen sulfate, a mixture of unsaturated aliphatic sulfonic acid and hydroxylated aliphatic sulfonic acid, hydrochloric acid, sulfuric acid, phosphoric acid, and so on, even though these acid catalysts are preferred, other acidic polymerization catalysts may be used, e.g. phosphonitrilic polymerization catalysts. Any catalyst can be used together as long as it can cause polymerization of the low molecular weight organosiloxane. Salts of these polymerization catalysts may be salts formed with the 1) alkali metal cations Li, Na, K, Rb, or Cs, 2) the alkaline earth metal cations; Mg, Ca, Sr, or Ba, 3) salts of ammonia compounds such as ammonia and various substituted amines and the like.

The anionic surfactant is not limited to those represented by the aforesaid formulas. One kind or a mixture of two kinds or more is usable, for example, polyoxyethylene alkylether sulfuric ester or salt thereof such as polyoxyethylene (4) laurylethersulfate, polyoxyethylene(13) cetylethersulfate, polyoxyethylene(6) stearylethersulfate, polyoxyethylene(4) sodium laurylethersulfate, polyoxyethylene(4) ammonium octylphenylethersulfate; polyoxyethylene alkylether carboxylate ester or salt thereof such as polyoxyethylene(3) laurylethercarboxylate, polyoxyethylene(3)stearylethercarboxylate, polyoxyethylene(6) sodium laurylethercarboxylate, and polyoxyethylene(6) sodium octylethercalboxylate; and so on.

A usage amount of the anionic surfactant is 0.5 to 20 parts by weight (preferably 0.5 to 10 parts by weight) relative to the total amount 100 parts by weight of colloidal silica constituting the cores and organosiloxane constituting the shells. Inferior stability of the produced emulsion may possibly cause separation with the usage amount of less than 0.5 parts by weight, while the usage amount of more than 20 parts by weight may cause viscosity increase of the produced emulsion to lower its fluidity. Incidentally, in the case of using the polymerization catalyst together, the amount of the polymerization catalyst used together is preferably about 0.05 to about 10 parts by weight relative to the total 100 parts by weight of colloidal silica and organosiloxane.

Meanwhile, an example of the cationic surfactant is a quaternary ammonium surfactant represented by the following general formula $R^{59}N^{\oplus}(R^{60})(R^{61})(R^{62})$ $X^-$; where, $R^{59}$ is aliphatic monovalent hydrocarbon group with the number of carbon atoms thereof being 6 or 22, preferably 8 to 18, each of $R^{60}$, $R^{61}$, and $R^{62}$ is a monovalent hydrocarbon of 1 to 3 carbons, and X is a hydroxyl group, a sulfate group, chlorine atom, or a bromine atom).

Specific examples of $R^{59}$ are hexyl, octyl, decyl, dodecyl, cetyl, stearyl, myricyl, oleyl, nonenyl, octynil, phytyl, pentadecadienyl, and so on. $R^{60}$, $R^{61}$, and $R^{62}$ are independently selected from a monovalent hydrocarbon group of 1 to 3 carbons; and an alkyl group such as vinyl and allyl; an aryl group such as phenyl, xenyl, and a naphthyl group; a cycloalkyl group such as cyclohexyl. [0038] Specific examples of the aforesaid quaternary ammonium surfactant are laurylytrimethylammonium sulfate, laurylytrimethylammonium chloride, stearyltrimethylammonium chloride, cetyltrimethylammonium chloride, dicocoyldimethylammonium chloride, distearyldimethylammonium chloride, benzalkonium chloride, stearyldimethylbenzylammonium chloride.

A usage amount of the cationic surfactant is 0.5 to 3 wt. %, preferably 0.5 to 1 wt. %.

The cationic colloidal silica core/silicone shell particles manufactured through the use of a method described in Japanese Patent Laid-open No. Hei 9-137062 can be used. Specifically, in this method emulsion polymerization is caused using an anionic surfactant and after the reaction is finished, a nonionic surfactant and/or an amphoteric surfactant are (is) added as a miscible surfactant, and a cationic surfactant is further added for conversion to cationic properties.

A silicone emulsion containing the colloidal silica core/silicone shell particles produced in such emulsion polymerization is a very stable emulsion. It especially exhibits good blend stability when being blended into water-based hair care cosmetics such as shampoo, hair rinse, hair conditioner, a hair treatment product, and a hair styling product.

The polyalkyleneoxide modified trisiloxane mentioned above can be manufactured by well known methods.

Specific examples of the nonionic surfactant are polyoxyethylene alkyl ether such as polyoxyethylene (6) laurylether, polyoxyethylene (7) cetylether, polyoxyethylene(20) stearylether, and polyoxyethylene(10) behenylether; polyoxyethylene alkylphenyl ether such as polyoxyethylene(3) octylphenylether and polyoxyethylene (18)nonylphenyl ether; polyethyleneglycol fatty acid ester such as polyethylene glycol monostearate (14EO) and polyethyleneglycol distearate (80EO); polyoxyethylene sorbitan fatty acid ester such as polyoxyethylene sorbitan monostearate (20EO), polyoxyethylene sorbitan monolaurate (6EO), polyoxyethylene sorbitan monopalmitate (20EO), polyoxyethylene sorbitan monostearate (6EO), and polyoxyethylene sorbitan trioleate (20EO); sorbitan fatty acid ester such as sorbitan monopalmitate and coconut oil fatty acid sorbitan; polyoxyethyleneglycerol fatty acid ester such as polyoxyethylene hydrogenated castor oil, polyoxyethylene sorbit tetraoleate, polyoxyethylene monooleate(15)glyceryl, and polyoxyethylene monostearate(15)glyceryl; polyoxyethylene polyoxypropylene alkyl ether such as polyoxyethylenephytosterol and polyoxyethylene(10) polyoxypropylene(4)cetylether; polyoxyethylene alkylamine such as polyoxyethylene(5) stearylamine; and polyoxyethylene alkylether phosphate such as polyoxyethylene(5) sodium cetylether phosphate.

Among these nonionic surfactants, those whose HLB is 6 to 20 is preferably used together since the resultant core/shell particles has a good emulsion stability.

The hair care cosmetic composition according to the present invention has as its essential components the core/shell particles and polyorganosiloxane, the shell particles consisting of colloidal silica serving as the cores and the shells of silicone covering the cores by way of silicon bonding. Accordingly, the action of the colloidal silica core/silicone shell particles gives satisfactory setting retention to hair, and in addition, the co-usage of colloidal silica core/silicone shell particles and polyorganosiloxane enables to give a smoother feeling than that brought about by the single use of polyorganosiloxane.

Specific examples of the hair care cosmetic composition according to the present invention are shampoo, hair rinse, hair conditioner, a hair treatment product, a hair styling product, hair mousse, hair cream, hair gel, and so on.

When the colloidal silica core/silicone shell particles of the present invention are used as a hair rinse agent, it is preferable to use one kind or two kinds or more of quaternary ammonium salt in the hair care cosmetic composition at a ratio of 0.1 wt % to 5 wt %. The ratio less than 0.1 wt % does not give a satisfactory rinse effect while the ratio more than 5 wt % results in high viscosity hair cosmetics, which is not suitable for use.

Examples of the quaternary ammonium salt are cetyltrimethylammonium chloride, stearyltrimethylammonium chloride, behenyltrimethylammonium chloride, behenyldimethylhydroxyethylammonium chloride, stearyldimethylammonium chloride, cetyltriethylammonium methylsulfate, and so on. Among them, stearytrimethylammonium chloride, behenyltrimethylammonium chloride, and stearyldimethylbenzylammonium chloride are especially preferable.

Meanwhile, when the colloidal silica core/silicone shell particles of the present invention are used for a washing agent such as shampoo, it is preferable that one kind or two kinds or more of the following is (are) used in hair cosmetic at a ratio of 5 wt % to 40 wt. %: an anionic surfactant such as fatty acid soap, a-acyl sulfonate, alkyl sulfonate, alkylnaphthalene sulfonate, alkyl sulfate, polyoxyethylenealkylether sulfate, alkylamide sulfate, alkyl phosphate, alkylamide phosphate, alkyloylalkyltaurine salt, and N-acylamino acid salt; a nonionic surfactant such as glycerol fatty acid ester, for example, glycerol monostearate, glycerol monooleate, and so on, sorbitan fatty acid ester, for example, sorbitan stearate, sorbitan oleate, and so on, polyoxyethylene sorbitan fatty acid ester, for example, polyoxyethylene coconut oil fatty acid sorbitan, polyoxyethylene sorbitan monopalmetate, polyoxyethylene sorbitan monostearate, and so on, polyoxyethylene alkylether, for example, polyoxyethylenelaurylether, polyoxyethylenestearylether, and so on, polyoxyethyleneglycol fatty acid ester, for example, polyoxyethyleneglycol monolaurate, polyethyleneglycol distearate, glycol distearate, and so on, and alkylalkanolamide, for example, diethanolamide laurate, coconut oil fatty acid diethanolamide, and so on; and an amphoteric surfactant such as betaine, for example, betaine lauryldimethylaminoacetate, betaine stearyldimethylaminoacetate, 2-alkyl-N-carboxymethyl-N-hydroxyethylimidazolinium betaine, coconut oil fatty acid amide propyl betaine, amidepropyl betaine laurate, and so on, aminocarboxylate, and imidazoline derivative. The ratio of these surfactants less than 5 wt % results in inferior washability and inferior foaming in washing, while the ratio more than 40 wt % results in high viscosity of the obtained hair cosmetic, which is not suitable for use.

It is permissible to blend the following in the hair care cosmetic composition of the present invention according to its intended use, that is, oil such as fluid paraffin, squalane, lanolin derivative, higher alcohol, and various kinds of ester oil; water-soluble oil such as ethyleneglycol, propyleneglycol, glycerol, and sorbitol polyethyleneglycol; moisturizer such as hyaluronic acid, chondoroitin acid, and pyrrolidone carboxylate; a thickener such as carboxy vinyl polymer; a cationic high polymer such as cation-denatured cellulose ether derivative, polyvinylpyrrolidone derivative quaternary ammonium, diallyl dimethylammonium chloride, polyamide derivative quaternary ammonium, polyoxyethylene polyalkylene, and polyamine; an ultraviolet absorbent; odor; and so on.

Uses for the Compositions of the Present Invention:

A. Hair Care Applications

The composition of the present invention may be used as an additive to provide hair styling benefits, including, but not limited to enhanced curl retention, smoothness, low tack and quick drying time, frizz control.

B. Skin Care Applications

In a preferred embodiment skin care active ingredients in both water soluble and water insoluble forms can be added to the composition. Said ingredients may include fat soluble vitamins, sunscreens and pharmaceutically active ingredients. These skin care active ingredients include glycerin, zinc oxide; chamomile oil; ginko biloba extract; pyroglutamic acid, salts or esters; sodium hyaluronate; 2-hydroxyoctanoic acid; sulfur; salicylic acid; carboxymethyl cysteine, water, propylene glycol and mixtures thereof.

Complimentary products may be used in conjunction with the present invention to compliment the composition and improve its aesthetic appeal to the user.

There are a great number of other ingredients approved for use in the cosmetic art that may be used in compositions of the present invention. Such ingredients are those approved for use in cosmetics and can be found listed in reference books such as the CTFA Cosmetic Ingredient Handbook. Said ingredients include waxes, fragrances, flavor oils, skin care ingredients such as sunscreen, emulsifiers and the like. Hypoallergenic compositions can be made into the present invention where said compositions do not contain fragrances, flavor oils, lanolin, sunscreens, particularly PABA, or other sensitizers and irritants.

Other materials may be included to provide the product form desired by the consumer. Such forms include liquids, pastes, and solids. In the case of a solid form, the composition of the present invention comprises materials in a sufficient amount so as to form a stable stick. These materials are herein referred to as solid formers. Said solid formers are preferably used at levels from about 0.5% to about 35.0% more preferably from about 7.0% to about 25.0%, and most preferably from about 8% to about 20.0% of the composition. Said solid formers are selected from the group consisting of solid polyol fatty acid polyesters, waxes, solid oils and mixtures thereof.

The following optional ingredients can be present in various quantities. The object of the present invention may be formulated with optional components, such as fragrances, emollient, solvents, humectants, optical brighteners, thickeners, powders, viscosity modifiers, hydrotropes, preservatives, bluing agents, and dyes, to produce a wide variety of end use products.

Although the use of such optional components is not essential to the present invention, and may in fact be somewhat less preferred depending on the desired final formulation and end use application, suitable optional emollients useful in formulating with blends of the present invention include, for example, stearyl alcohol, glyceryl ricinoleate, glyceryl stearate, propane-1,2-diol, butane-1,3-diol, mink oil, cetyl alcohol, stearamidopropyl dimethylamine, isopropyl isostearate, stearic acid, isobutyl palmitate, isocetyl stearate, oleyl alcohol, isopropyl laurate, hexyl laurate, decyl oleate, octadecan-2-ol, isocetyl alcohol, eicosanyl alcohol, behenyl alcohol, cetyl palmitate, silicone oils such as dimethylpolysiloxane, dimethicone copolyols, di-n-butyl sebacate, isopropyl myristate, isopropyl palmitate, isopropyl stearate, butyl stearate, polyethylene glycol, triethylene glycol, lanolin, cocoa butter, corn oil, cotton seed oil, tallow, lard, olive oil, palm kernel oil, rapeseed oil, safflower seed oil, soybean oil, sunflower seed oil, olive oil, sesame seed oil, coconut oil, arachis oil, castor oil, acetylated lanolin alcohols, petrolatum, mineral oil, butyl myristate, isostearic acid, palmitic acid, isopropyl linoleate, lauryl lactate, myristyl lactate, decyl oleate, and myristyl myristate, and mixtures thereof.

Although generally less preferred, optional solvents useful in formulating with blends of the present invention include, for example, ethyl alcohol, propylene glycol, water, isopropanol, castor oil, ethylene glycol monoethyl ether, diethylene glycol monobutyl ether, diethylene glycol monoethyl ether, dimethyl sulphoxide, dimethyl formamide, and tetrahydrofuran, and mixtures thereof.

Optional humectants useful in formulating with blends of the present invention include, for example, glycerin, sorbitol, sodium 2-pyrrolidone-5-carboxylate, soluble collagen, dibutyl phthalate, propylene glycol, and gelatin, and mixtures thereof.

Optional swellable polymer thickening agents include, for example, methyl cellulose, ethyl cellulose, xanthan gum, gum arabic, gum karaya, guar gum, locust bean gum, ghatti gum, hydrolyzed starches, low molecular weight ethylene oxide polymers, low molecular weight propylene oxide polymers and mixtures thereof.

Optional non-volatile, nonionic silicone conditioning agents suitable for the present invention are selected from the group comprising polyalkyl siloxanes, polyaryl siloxanes, polyalkylaryl siloxanes, polyether siloxane copolymers and mixtures thereof. However, it should also be noted that any silicone fluid having hair conditioning properties may used as an optional ingredient in the present Compositions. The polyether siloxane copolymers that may be used include, for example, a polypropylene oxide modified dimethylpolysiloxane although ethylene oxide or mixtures of ethylene oxide and propylene oxide may also be used.

The optional pearlescent/suspending agents suitable for use in the present invention include any of several long chain acyl derivative materials or mixtures of such materials, such as long chain acyl derivatives, long chain amine oxides, and mixtures thereof, wherein such suspending/pearlescent agents are present in the composition in crystalline form. These pearlescent/suspending agents are described in U.S. Pat. No. 4,741,855, Grote and Russell, issued May 3, 1988, the disclosure of which is incorporated herein by reference in its entirety. Included are ethylene glycol esters of fatty acids having from about 16 to about 22 carbon atoms. Preferred are the ethylene glycol stearates, both mono- and distearate, but particularly the distearate containing less than about 7% of the monostearate. Other suspending agents found useful are alkanolamides, preferably with about 16 to about 18 carbon atoms. Preferred alkanolamides are stearic monoethanolamide, stearic diethanolamine, stearic monoisopropanolamide and stearic monoethanolamide stearate. Other long chain acyl derivatives include long chain esters of long chain fatty acids (e.g., stearyl stearate, cetyl palmitate, etc.); glyceryl esters (e.g., glyceryl distearate) and long chain ester of long chain alkanol amides (e.g., stearamide DEA distearate, stearamide MEA stearate).

Additional optional pearlescent/suspending agents suitable for use in the present invention are alkyl ($C_{18}$-$C_{22}$) dimethyl amine oxides, such as stearyl dimethyl amine oxide. If the compositions contain an amine oxide or a long chain acyl derivative as a surfactant the pearlescent/suspending function could also be provided by such surfactant and additional pearlescent/suspending agents may not be needed.

Further optional pearlescent/suspending agents that can be used are long chain acyl derivatives, including, for example, N,N-dihydroxycarbyl amido benzoic acid and soluble thereof (e.g., Na and K salts), particularly N,N-di(hydrogenated)$C_{16}$, $C_{18}$ and tallow amido benzoic acid species of this family, which are commercially available from Stepan Company (Northfield, Ill., USA).

Another type of pearlescent/suspending agent which can be used in the present invention is xanthan gum. Xanthan gum is well known to those skilled in the art. For example, hair care compositions utilizing xanthan gum as a pearlescent/suspending agent for the silicone hair conditioning component are described in U.S. Pat. No. 4,788,066, Bolich and Williams, issued Nov. 29, 1988, the disclosure of which is incorporated herein by reference in its entirety. See also, Whistler, Roy L. Editor Industrial Gums—Polysaccharides and Their Derivatives, New York: Academic Press, 1973. Xanthan gum is commercially available from Kelco, a division of Merck & Co., Inc. as Keltrol.

Combinations of long chain acyl derivatives and xanthan gum are disclosed as pearlescent/suspending agents for silicone hair conditioners in U.S. Pat. No. 4,704,272, Oh et al., issued Nov. 3, 1987, both of which are incorporated herein by referenced in their entirety, and may also be used in the present compositions. Gel formulations have high levels of pearlescent/suspending agents relative to pourable, liquid formulations which used as the primary means of imparting gel-like viscosity. Optional gelling agents suitable for use in the present invention include, for example, hydroxy ethylcellulose.

Other optional conditioning agents include sucrogyleride materials, particularly those disclosed in U.S. Pat. No. 5,705,147, issued Jan. 6, 1998 to Stepan Company, incorporated herein in its entirety.

Optional powders useful in formulating with blends of the present invention include, for example, chalk, talc, fullers earth, kaolin, starch, gums, colloidal silicon dioxide, sodium polyacrylate, tetra alkyl and/or trialkyl aryl ammonium smectites, chemically modified magnesium aluminum silicate, organically modified montmorillonite clay, hydrated aluminum silicate, fumed silica, carboxyvinyl polymer, cellulosics such as hydroxyethyl cellulose and sodium carboxymethyl cellulose, ethylene glycol monostearate, zinc or magnesium stearate, zinc oxide and magnesium oxide, and mixtures thereof. These components may also be used as thickeners in fluid or semi-fluid compositions.

Examples of other optional ingredients useful in formulating with blends of the present invention include, for example, volatile and non-volatile silicones; silicone polymers; preservatives, such as para-hydroxy benzoate esters; humectants, such as butane-1,3-diol, glycerol, sorbitol, polyethylene glycol; stabilizers, such as sodium chloride or ammonium chloride; buffer systems, such as lactic acid together with a base such as sodium hydroxide; oils and waxes, such as avocado oil, Evening Primrose oil, mineral oil, petrolatum, sunflower oil, beeswax, ozokerite wax, paraffin wax, lanolin, lanolin alcohol; emollients; thickeners; activity enhancers; colorants; whiteners; fragrances; and bactericides, and mixtures thereof.

The blends of the present invention may also be formulated with optional detergent builder materials. Nearly any detergent builders known in the art can be formulated with the present blends. Examples of useful detergent builders are described in U.S. Pat. Nos. 4,321,165, (to Smith et al, issued Mar. 23, 1982) and 5,565,145 (to Watson et al., issued Oct. 15, 1996), both incorporated herein by reference. Detergent builders can optionally be included in the compositions herein to assist in controlling mineral hardness. Inorganic as well as organic builders can be used. Builders are typically used in fabric laundering compositions to assist in the removal of particulate soils. The level of builder can vary widely depending upon the end use of the composition and its desired physical form. When present in a final formulation, the compositions will typically comprise at least about 1% builder. Liquid formulations typically comprise from about 5% to about 50%, more typically about 5% to about 30%, by weight, of detergent builder. Granular finished formulations typically comprise from about 10% to about 80%, more typically from about 15% to about 50% by weight, of the detergent builder. Lower or higher levels of builder, however, also can be acceptable.

Enzymes and enzyme stabilizers can be formulated with blends of the instant invention for a wide variety of fabric laundering purposes, including removal of protein-based, carbohydrate-based, or triglyceride-based stains, for example, and for fabric restoration. Examples of useful enzymes and enzyme stabilizers are described in U.S. Pat. No. 5,565,145 (to Watson et al., issued Oct. 15, 1996), incorporated herein by reference. Useful enzymes include, for example, proteases, amylases, lipases, and cellulases, as well as mixtures thereof. Other types of enzymes may also be included. They may be of any suitable origin, such as vegetable, animal, bacterial, fungal and yeast origin. However, a particular enzyme choice is governed by several factors such as pH-activity and/or stability optima, thermostability, stability versus active detergents, builders and so on. In this respect bacterial or fungal enzymes are preferred, such as bacterial amylases and proteases, and fungal cellulases.

Suitable examples of proteases are the subtilisins which are obtained from particular strains of *B. subtilis* and *B. licheniforms*. Another suitable protease is obtained from a strain of *Bacillus*, having maximum activity throughout the pH range of 8-12, developed and sold by Novo Industries A/S under the registered trade name ESPERASE. The preparation of this enzyme and analogous enzymes is described in British Pat. Specification No. 1,243,784 of Novo. Proteolytic enzymes suitable for removing protein-based stains that are commercially available include those sold under the tradenames ALCALASE and SAVINASE by Novo Industries A/S (Denmark) and MAXATASE by International Bio-Synthetics, Inc. (The Netherlands). Other proteases include Protease A (see European Patent Application 130,756, published Jan. 9, 1985) and Protease B (see European Patent Application Ser. No. 87303761.8, filed Apr. 28, 1987, and European Patent Application 130,756, Bott et al, published Jan. 9, 1985).

Amylases include, for example, amylases described in British Patent Specification No. 1,296,839 (Novo), RAPIDASE, International Bio-Synthetics, Inc. and TERMAMYL, Novo Industries.

Cellulases suitable for use with ternary surfactant blends of the present invention include both bacterial or fungal cellulase. Preferably, they will have a pH optimum of between 5 and 9.5. Suitable cellulases are disclosed in U.S. Pat. No. 4,435,307, Barbesgoard et al, issued Mar. 6, 1984, which discloses fungal cellulase produced from *Humicola insolens* and *Humicola* strain DSM1800 or a cellulase 212-producing fungus belonging to the genus *Aeromonas*, and cellulase extracted from the hepatopancreas of a marine mollusk (Dolabella Auricula Solander). Suitable cellulases are also disclosed in GB-A-2.075.028; GB-A-2.095.275 and DE-OS.247. 832CAREZYME (Novo) is especially useful.

Suitable lipase enzymes include those produced by microorganisms of the *Pseudomonas* group, such as *Pseudomonas stutzeri* ATCC 19.154, as disclosed in British Patent. 1,372,034. See also lipases in Japanese Patent Application 53,20487, laid open to public inspection on Feb. 24, 1978. This lipase is available from Amano Pharmaceutical Co. Ltd., Nagoya, Japan, under the trade name Lipase P Amano, hereinafter referred to as Amano-P.

Other commercial lipases include Amano-CES, lipases ex Chromobacter viscosum, e.g. Chromobacter viscosum var. *lipolyticum* NRRLB 3673, commercially available from Toyo Jozo Co., Tagata, Japan; and further Chromobacter viscosum lipases from U.S. Biochemical Corp., U.S.A. and Diosynth Co., The Netherlands, and lipases ex *Pseudomonas gladioli*. The LIPOLASE enzyme derived from *Humicola lanuginosa* and commercially available from Novo (see also EPO 341, 947) is a preferred lipase for use herein.

A wide range of enzyme materials and means for their incorporation into synthetic detergent compositions are also disclosed in U.S. Pat. No. 3,553,139, issued Jan. 5, 1971 to McCarty et al. Enzymes are further disclosed in U.S. Pat. No. 4,101,457, Place et al, issued Jul. 18, 1978, and in U.S. Pat. No. 4,507,219, Hughes, issued Mar. 26, 1985, both. Enzyme materials useful for liquid detergent formulations, and their incorporation into such formulations, are disclosed in U.S. Pat. No. 4,261,868, Hora et al, issued Apr. 14, 1981. Enzymes for use in detergents can be stabilized by various techniques. Enzyme stabilization techniques are disclosed and exemplified in U.S. Pat. No. 3,600,319, issued Aug. 17, 1971 to Gedge, et al, and European Patent Application Publication No. 0 199 405, Application No. 86200586.5, published Oct. 29, 1986, Venegas. Enzyme stabilization systems are also described, for example, in U.S. Pat. No. 3,519,570.

The optional enzymes useful herein may be stabilized by the presence of water-soluble sources of calcium and/or magnesium ions in the finished compositions which provide such ions to the enzymes. Calcium ions are generally somewhat more effective than magnesium ions and are preferred herein if only one type of cation is being used. Additional stability can be provided by the presence of various other disclosed stabilizers, especially borate species. See Severson, U.S. Pat. No. 4,537,706. Typical detergents, especially liquids, will comprise from about 1 to about 30, preferably from about 2 to about 20, more preferably from about 5 to about 15, and most preferably from about 8 to about 12, millimoles of calcium ion per liter of finished composition. This concentration can vary somewhat, depending on the amount of enzyme present and its response to the calcium or magnesium ions. The level of calcium or magnesium ions should be selected so that there is always some minimum level available for the enzyme, after allowing for complexation with builders, fatty acids, etc., in the final composition. Any water-soluble calcium or magnesium salt can be used as the source of calcium or magnesium ions, including, but not limited to, calcium chloride, calcium sulfate, calcium maleate, calcium maleate, calcium hydroxide, calcium formate, and calcium acetate, and the corresponding magnesium salts. A small amount of calcium ion, generally from about 0.05 to about 0.4 millimoles per liter, is often also present in the final composition due to calcium in the enzyme slurry and formula water. In solid detergent compositions the final formulation may include a sufficient quantity of a water-soluble calcium ion source to provide such amounts in the laundry liquor. In the alternative, natural water hardness may suffice.

Generally, the aforementioned levels of calcium and/or magnesium ions are sufficient to provide enzyme stability to a finished formulation. More calcium and/or magnesium ions can be added to the compositions to provide an additional measure of grease removal performance. Accordingly, final formulations prepared from the blends disclosed herein typically will comprise from about 0.05% to about 2% by weight of a water-soluble source of calcium or magnesium ions, or both. The amount of water-soluble ion can vary with the amount and type of enzyme employed in the final composition.

Final compositions based on the blends detailed herein may also optionally contain various additional stabilizers, especially borate-type stabilizers. Boric acid is preferred, although other compounds such as boric oxide, borax and other borates (e.g., sodium ortho-, meta- and pyroborate, and sodium pentaborate) are suitable. Substituted boric acids (e.g., phenylboronic acid, butane boronic acid, and p-bromo phenylboronic acid) can also be used in place of boric acid.

Bleaching agents, bleach activators, chelating agents, anti-redeposition agents, polymeric dispersing agents, optical brighteners, suds suppressors, dye transfer inhibition agents, optical brighteners, and soil release agents can be formulated with blends of the instant invention. Examples of such materials are generally described in U.S. Pat. No. 5,565,145 (to Watson et al., issued Oct. 15, 1996), incorporated herein by reference.

Various other detergent additives or adjuvants may be present in the detergent product to give it additional desired properties, either of functional or aesthetic nature. Thus, there may be included in the formulation minor amounts of soil suspending or anti-redeposition agents, e.g. polyvinyl alcohol, fatty amides, sodium carboxymethyl cellulose, hydroxypropyl methyl cellulose; optical brighteners, e.g. cotton, amine and polyester brighteners, for example, stilbene, triazole and benzidine sulfone compositions, especially, sulfonated substituted triazinyl stilbene, sulfonated naphthotriazole stilbene, benzidine sulfone, etc., most preferred are stilbene and triazole combinations.

Bluing agents such as ultramarine blue; enzymes, preferably proteolytic enzymes, such as subtilisin, bromelin, papain, trypsin and pepsin, as well as amylase type enzymes; bactericides, e.g. tetrachlorosalicylanilide, hexachlorophene; fungicides; dyes; pigments (water dispersible); preservatives; ultraviolet absorbers; anti-yellowing agents, such as sodium carboxymethyl cellulose, complex of $C_{12}$ to $C_{22}$ alkyl alcohol with $C_{12}$ to $C_{18}$ alkylsulfate; pH modifiers and pH buffers; color safe bleaches, perfume, and anti-foam agents or suds suppressors, e.g. silicon compounds, can also be used.

In the case of final formulations, other optional ingredients include neutralizing agents, buffering agents, phase regulants, hydrotropes, polyacids, suds regulants, opacifiers, antioxidants, preservatives, bactericides, dyes, perfumes, and brighteners described in the U.S. Pat. No. 4,285,841, Barrat et al., issued Aug. 25, 1981, incorporated herein by reference. Other ingredients useful in final detergent compositions can be formulated with blends of the instant invention, including carders, processing aids, pigments, solvents for liquid formulations, solid fillers for bar compositions, sodium sulfate, sodium chloride, protein hydrolysates, cholesterol derivatives, UV absorbers, chelating agents, etc. If high sudsing is desired, suds boosters such as the $C_{10}$-$C_{16}$ alkanolamides can be incorporated into the final compositions, typically at 1%-10% levels. The $C_{10}$-$C_{14}$ monoethanol and diethanol amides illustrate a typical class of such suds boosters. If desired, soluble magnesium salts such as $MgCl_2$, $MgSO_4$, and the like, can be added at levels of, typically, 0.1%-2%, to provide additional suds and to enhance grease removal performance to a final formulation.

Additionally, the blends may contain non-conventional surfactants, such as fluorosurfactants, gemini surfactants and polymeric cationic and anionic surfactants. Blends of the present invention are prepared from readily available, economical raw materials, and generally their preparation does not require any special handling or equipment. The blends may be prepared in a batch mode or a continuous mode.

Suitable anti-dandruff agents are selected from the group comprising zinc pyrithione, selenium sulfide, sulfur, coal tar, zinc omadine, piroctone olamine and mixtures thereof.

Suitable preservatives are selected from the group comprising benzyl alcohol, methyl paraben, propyl paraben and imidazolidinyl urea.

Suitable thickeners and viscosity modifiers are selected from the group comprising diethanolamides of long chain fatty acids (e.g., PEG-3 lauramide), block polymers of ethylene oxide and propylene oxide such as Pluronic® F88 offered by BASF, Wyandotte, sodium chloride, sodium sulfate, ammonium xylene sulfonate, ethyl alcohol and polyhydridic alcohols such as, for example, propylene glycol and polyvinyl alcohol.

Suitable gelling agents include, for example, hydroxyethyl cellulose.

Suitable pH adjusting agents are selected from the group comprising citric acid, succinic acid, phosphoric acid, sodium hydroxide, sodium carbonate, etc.

Suitable sequestering agents include, for example, disodium ethylenediamine tetraacetate.

The ternary surfactant blends of the present invention typically contain water as the solvent; however, other solvents may optionally be employed, either alone or in combination with water. Low molecular weight primary or secondary alcohols, exemplified by methanol, ethanol, propanol, and isopropanol, are suitable optional solvents. Monohydric alcohols are preferred optional solvents, but polyols such as those containing from 2 to about 6 carbon atoms and from 2 to about 6 hydroxy groups (e.g., 1,3-propanediol, ethylene glycol, glycerine, and 1,2-propanediol) can also be used. The compositions may contain from about 5 to about 90 percent, typically from about 10 to about 50 percent by weight of water and/or optional solvent.

While pH is of secondary significance herein, the object of the present invention typically are prepared having a pH of between about 2 and about 10, preferably between about 5 and about 8. Techniques for controlling pH at recommended usage levels include the use of buffers, alkalis, acids, etc., and are well known to those skilled in the art. Suitable materials for adjusting the pH of these compositions include triethanolamine, diethanolamine, sodium carbonate, sodium bicarbonate, and the like.

Ternary surfactant blends of this invention may be formulated into commercially useful products. Ternary surfactant blends of the invention are preferably clear and exhibit no precipitate formation upon aging.

Additionally, the ternary surfactant blends may be processed into a variety of forms such as, for example, liquids, solutions, solids, powders, flakes, semi-solids, gels, "ringing" gels, G-phase liquids/pastes, hexagonal liquid crystal phases, or thick non-flowable pastes. The ternary surfactant blends may be spray dried, flaked, or extruded. Although not critical to the present invention, the blends may be prepared "neat" or in a conventional solvent such as water, low molecular weight alcohol or hydrocarbon, or a mixture thereof, to produce a solution of the ternary surfactant blend. The present invention encompasses ternary surfactant systems in dry form and as aqueous solutions. Ternary surfactant blends in concentrations up to 100 percent by weight may be isolated by drying a solution of the blend. Conversely, ternary surfactant blend solutions may be prepared by dissolving a solid form of the blend in water, low molecular weight alcohol, low molecular weight glycol, or mixtures thereof.

The inclusion of the film-forming polymer in the compositions of our invention provides the additional advantage of an enhanced sensory impression of the perfume because of the increased duration of its release from the treated surface.

i. Home Care Applications

Home care applications include laundry detergent and fabric softener, dishwashing liquids, wood and furniture polish, floor polish, tub and tile cleaners, toilet bowl cleaners, hard surface cleaners, window cleaners, antifog agents, drain cleaners, auto-dish washing detergents and sheeting agents, carpet cleaners, prewash spotters, rust cleaners and scale removers.

B. Agricultural Uses for the Composition—Pesticides—Agriculture, Horticulture, Turf, Ornamental and Forestry:

Many pesticide applications require the addition of an adjuvant to the spray mixture to improve coverage on foliar surfaces. Often that adjuvant is a surfactant or a polymer, which can perform a variety of functions, such as increasing spray droplet retention on difficult to wet leaf surfaces, enhance spreading to improve spray coverage, or to provide penetration of the herbicide into the plant cuticle, or to act as a film former to assist with even distribution of agrochemicals on foliar or seed surfaces. These adjuvants are provided either as a tank-side additive or used as a component in pesticide formulations.

Typical uses for pesticides include agricultural, horticultural, turf, ornamental, home and garden, seed protection, veterinary and forestry applications.

The composition of the present invention may also include at least one pesticide. The organomodified trisiloxane surfactant of the present invention is present at an amount sufficient to deliver between 0.005% and 2% to the final use concentration, either as a concentrate or diluted in a tank mix. Optionally the pesticidal composition may include excipients, co-surfactants, solvents, foam control agents, deposition aids, drift retardants, biologicals, micronutrients, fertilizers and the like. The term pesticide means any compound used to destroy pests, e.g., rodenticides, insecticides, miticides, fungicides, and herbicides. Illustrative examples of pesticides which can be employed include, but are not limited to, growth regulators, photosynthesis inhibitors, pigment inhibitors, mitotic disrupters, lipid biosynthesis inhibitors, cell wall inhibitors, and cell membrane disrupters. The amount of pesticide employed in compositions of the invention varies with the type of pesticide employed. More specific examples of pesticide compounds that can be used with the compositions of the invention are, but not limited to, herbicides and growth regulators, such as: phenoxy acetic acids, phenoxy propionic acids, phenoxy butyric acids, benzoic acids, triazines and s-triazines, substituted ureas, uracils, bentazon, desmedipham, methazole, phenmedipham, pyridate, amitrole, clomazone, fluridone, norflurazone, dinitroanilines, isopropalin, oryzalin, pendimethalin, prodiamine, trifluralin, glyphosate, glufosinate, sulfonylureas, imidazolinones, pyridinecarboxylic acids, clethodim, diclofop-methyl, fenoxaprop-ethyl, fluazifop-p-butyl, haloxyfop-methyl, quizalofop, sethoxydim, dichlobenil, isoxaben, and bipyridylium compounds.

Fungicide compositions that can be used with the present invention include, but are not limited to, aldimorph, tridemorph, dodemorph, dimethomorph; flusilazol, azaconazole, cyproconazole, epoxiconazole, furconazole, propiconazole, tebuconazole and the like; imazalil, thiophanate, benomyl carbendazim, chlorothialonil, dicloran, trifloxystrobin, fluoxystrobin, dimoxystrobin, azoxystrobin, furcaranil, prochloraz, flusulfamide, famoxadone, captan, maneb, mancozeb, dodicin, dodine, and metalaxyl.

Insecticide, larvacide, miticide and ovacide compounds that can be used with the composition of the present invention, but not limited to, *Bacillus thuringiensis*, spinosad, abamectin, doramectin, lepimectin, pyrethrins, carbaryl, primicarb, aldicarb, methomyl, amitraz, boric acid, chlordimeform, novaluron, bistrifluoron, triflumuron, diflubenzuron, imidacloprid, diazinon, acephate, endosulfan, kelevan, dimethoate, azinphos-ethyl, azinphos-methyl, izoxathion, chlorpyrifos, clofentezine, lambda-cyhalothrin, permethrin, bifenthrin, cypermethrin and the like.

The pesticide may be a liquid or a solid. If a solid, it is preferable that it is soluble in a solvent, or the organomodified trisiloxanes of the present invention, prior to application, and the silicone may act as a solvent, or surfactant for such solubility or additional surfactants may perform this function.

Agricultural Excipients:

Buffers, preservatives and other standard excipients known in the art also may be included in the composition.

Solvents may also be included in compositions of the present invention. These solvents are in a liquid state at room temperature. Examples include water, alcohols, aromatic solvents, oils (i.e. mineral oil, vegetable oil, silicone oil, and so forth), lower alkyl esters of vegetable oils, fatty acids, ketones, glycols, polyethylene glycols, diols, paraffinics, and so forth. Particular solvents would be 2,2,4-trimethyl, 1-3-pentane diol and alkoxylated (especially ethoxylated) versions thereof as illustrated in U.S. Pat. No. 5,674,832 herein incorporated by reference, or n-methyl-pyrrilidone.

Co-Surfactants:

Moreover, other co-surfactants, which have short chain hydrophobes that do not interfere with superspreading as described in U.S. Pat. Nos. 5,558,806; 5,104,647; and 6,221,811 are herein included by reference.

The co-surfactants useful herein include nonionic, cationic, anionic, amphoteric, zwitterionic, polymeric surfactants, or any mixture thereof. Surfactants are typically hydrocarbon based, silicone based or fluorocarbon based.

Useful surfactants include alkoxylates, especially ethoxylates, containing block copolymers including copolymers of ethylene oxide, propylene oxide, butylene oxide, and mixtures thereof, alkylarylalkoxylates, especially ethoxylates or propoxylates and their derivatives including alkyl phenol ethoxylate; arylarylalkoxylates, especially ethoxylates or propoxylates. and their derivatives; amine alkoxylates, especially amine ethoxylates; fatty acid alkoxylates; fatty alcohol alkoxylates; alkyl sulfonates; alkyl benzene and alkyl naphthalene sulfonates; sulfated fatty alcohols, amines or acid amides; acid esters of sodium isethionate; esters of sodium sulfosuccinate; sulfated or sulfonated fatty acid esters; petroleum sulfonates; N-acyl sarcosinates; alkyl polyglycosides; alkyl ethoxylated amines; and so forth.

Specific examples include alkyl acetylenic diols (SURFONYL-Air Products), pyrrilodone based surfactants (e.g., SURFADONE-LP 100-ISP), 2-ethyl hexyl sulfate, isodecyl alcohol ethoxylates (e.g., RHODASURF DA 530-Rhodia), ethylene diamine alkoxylates (TETRONICS-BASF), and ethylene oxide/propylene oxide copolymers (PLURONICS-BASF) and Gemini type surfactants (Rhodia).

Preferred surfactants include ethylene oxide/propylene oxide copolymers (EO/PO); amine ethoxylates; alkyl polyglycosides; oxo-tridecyl alcohol ethoxylates, and so forth.

In a preferred embodiment, the agrochemical composition of the present invention further comprises one or more agrochemical ingredients. Suitable agrochemical ingredients include, but not limited to, herbicides, insecticides, growth regulators, fungicides, miticides, acaricides, fertilizers, biologicals, plant nutritionals, micronutrients, biocides, paraffinic mineral oil, methylated seed oils (i.e. methylsoyate or methylcanolate), vegetable oils (such as soybean oil and canola oil), water conditioning agents such as Choice® (Loveland Industries, Greeley, Colo.) and Quest (Helena Chemical, Collierville, Tenn.), modified clays such as Surround® (Englehard Corp.), foam control agents, surfactants, wetting agents, dispersants, emulsifiers, deposition aids, anti-drift components, and water.

Suitable agrochemical compositions are made by combining, in a manner known in the art, such as, by mixing one or more of the above components with the organomodified trisiloxane of the present invention, either as a tank-mix, or as an "In-can" formulation. The term "tank-mix" means the addition of at least one agrochemical to a spray medium, such as water or oil, at the point of use. The term "In-can" refers to a formulation or concentrate containing at least one agrochemical component. The "In-can" formulation may then diluted to use concentration at the point of use, typically in a Tank-mix, or it may be used undiluted.

PREPARATION EXAMPLES

Example 1

Preparation of a Silicone Emulsion-1

A mixing vessel was charged with 1696.8 g of deionized water and 18.0 g of dodecylbenzenesulfonic acid (DDBSA), 257.2 g of octamethylcyclotetrasiloxane and 514.4 g of silica dispersion Nyacol 9950 (from Akzo Nobel). Contents were mixed for 5 minutes and passed through a rotor-stator homogenizer to yield an emulsion having pH=2.0 and an average particle size 0.49 μm.

The pre-formed emulsion was placed in the Ross Mixer, agitated with the anchor blade and heated to 80° C. for 5 hours. Then the emulsion was cooled to room temperature and mixing continued for 15 more hours followed by neutralization with 5.6 g of triethanolamine.

Final emulsion with following properties was obtained:

| Appearance: | milky |
|---|---|
| Viscosity: | 6.0 cps |
| Solids: | 19.2% |
| pH: | 7.0 |
| Particle size: | 0.12 μm |
| $D_4$ content: | 0.4% |

Example 2

Preparation of a Silicone Emulsion-2

Deionized water (172.57 g, 9.59 mol) and sodium dodecylsulfate (2.50 g, 0.0087 mol) was added to a 500 mL beaker. Nyacol 9950 (49.95, 50% silica), decamethylcyclopentasiloxane (24.98 g, 0.067 mol) and concentrated sulfuric acid (0.1 mL) was added to the beaker. The mixture was stirred with a magnetic stirrer for 15 minutes until homogenous. The white solution was homogenized by passing the fluid through a Microfluidics Microfluidizer Processor, model M110S, 3 times at 80 psi. Following homogenization the fluid was added into a 500 mL 4 neck round bottom flask equipped with a nitrogen blanket, overhead stirrer, and a thermocouple. The flask was heated via a heating mantle and a temperature controller to 80° C. for 5 hours. The flask was allowed to cool to room temperature and was stirred for an additional 16 hours. The flask was neutralized to pH 7.08 using triethanolamine.

Physical Properties:

| Appearance: | White Milky Fluid |
|---|---|
| % Non-volatile: | 17.6% |
| Particle Size: | 0.166 μm |
| Viscosity (25° C.): | 3.65 cSt |

Example 3

Preparation of Silicone Film Forming Emulsion-1A

An example of the composition of the present invention was prepared by combining Emulsion-1 with Silsoft 305, a trisiloxane alkoxylate of the general structure:

$$M^1_e D^1_f D^2_g M^2_h$$

where f is 0, g is 1; $R^7$, $R^8$, $R^9$, $R^{10}$, $R^{11}$, $R^{12}$ and $R^{16}$ are methyl; $R^{15}$ is a polyalkyleneoxide group of the general structure:

$$C_3H_8O(C_2H_4O)_j(C_3H_6O)_k(C_4H_8O)_m-H$$

where m is 0, and the sum of j+k+m satisfies the following relationship:

$$4 \geq j+k+m \leq 20;$$

Therefore, a mixing vessel was charged with 990.0 g of Emulsion-1 and 10 g of Silsoft 305 and contents were mixed for 1 hour.

The resulting emulsion gave the following properties:

| Appearance: | Milky |
|---|---|
| Viscosity: | 6.0 cps |
| Solids: | 19.2% |
| pH: | 7.0 |
| Surface tension: | 24.8 mN/m |

Example 4

Preparation of Silicone Film Forming Emulsion-2A

Another example of the composition of the present invention was prepared by combining 99.0 g of Emulsion-2 with 1.0 g of trisiloxane alkoxylate Silsoft 305. The solution was stirred for 1 hour to ensure complete dispersion.

The resulting composition gave the following Physical Properties:

| | |
|---|---|
| Appearance: | White Milky Fluid |
| % Non-volatile: | 18.5% |
| Particle Size: | 0.186 μm |
| Viscosity (25° C.): | 3.92 cSt |

Example 5

The evaluation of hair setting retention was made in such a manner that hair being 2 g in weight and 16 cm in length were rinsed in warm water at 40° C. for 30 seconds. This hair was wound around a curler being 1.4 centimeter in the outer diameter and dried with warm air at 40° C. for 30 minutes and allowed to cool to room temperature for 30 minutes. Subsequently hair was removed from the curler and given a uniform spray of each style retention fixative, which was prepared according to Table 1. The hair was allowed to dry under ambient conditions overnight.

TABLE 1

Hair Fixative Formulations

| Component | Hair Fixative 1 | Hair Fixative A | Hair Fixative B |
|---|---|---|---|
| Ethanol | 25.8 | 47.5 | 40 |
| Water | 40 | 47.5 | 40 |
| Butylene Glycol | 5 | 5 | 5 |
| Silicone Emulsion-1A | 29.2 | 0 | 0 |
| Polyquaternium 72 | 0 | 0 | 15 |

The hair at a length of L1 was hung vertically in an atmosphere at a temperature of 25° C. and a relative humidity of 90% and a length L2 was measured subsequently at 15 minute intervals. Percent curl retention was calculated based on the following formula where L=16 cm, and L1 was the hair before expose and L2 was the length of hair after exposure: %=(16−L2)/(16−L1)×100, and the results are shown in Table 2.

TABLE 2

Curl Retention

| Hair Fixative | Initial | 30 min. | 45 min. | 60 min. | 75 min. | 90 min. | 105 min. | 120 min |
|---|---|---|---|---|---|---|---|---|
| 1 | 100 | 45 | 37.5 | 37.5 | 37.5 | 37.5 | 37.5 | 37.5 |
| A | 100 | 27 | 17 | 9 | 0 | 0 | 0 | 0 |
| B | 100 | 33 | 29 | 29 | 19 | 19 | 5 | 5 |

Example 6

The evaluation of tack time and dry time was made in such a manner that hair being 2 g in weight and 16 cm in length was suspended vertically from a fixed position and a controlled amount of hair fixative which was prepared according to Table 1 was applied to the front of the hair, and a controlled amount of hair fixative was applied to the back of the hair. A timer was started and an evaluator felt the entire length of the tress with fingertips and indicated (a) when the hair started being sticky, (b) stopped being sticky, and (c) was completely dry. The drying time and duration of the sticky or tacky period can therefore be calculated and the results of the evaluation are shown in Table 3.

TABLE 3

Effect of Formulation on Tack and Dry Time

| Hair Fixative | Tack-time (sec.) | Dry Time (sec.) |
|---|---|---|
| Hair Fixative-1 | 2 | 23 |
| Hair Fixative-A | 2 | 13 |
| Hair Fixative-B | 47 | 87 |

Example 7

Conditions were similar to Example 5, however, using ethanol free formulations as described in Table 4. The improvement in curl retention is demonstrated in Table 5, where Hair Fixatives 2 and 3 show that greater curl retention is achieved with these compositions relative to Comparative examples Hair Fixative-A and Hair Fixative-B (Example 5, Table-2).

TABLE 4

Alcohol Free Hair Fixative Formulations

| Component | HAIR FIXATIVE-2 | HAIR FIXATIVE-3 |
|---|---|---|
| Water | 45.1 | 45.1 |
| AMP-95 | 0.6 | 0.6 |
| 2% Carbomer Soln | 25 | 25 |
| Silicone Emulsion 1A | 29.3 | 0 |
| Silicone Emulsion 2A | 0 | 29.3 |

TABLE 5

| | | | | CURL RETENTION | | | | |
|---|---|---|---|---|---|---|---|---|
| Hair Fixative | Initial | 30 min. | 45 min. | 60 min. | 75 min. | 90 min. | 105 min. | 120 min |
| 2 | 100 | 63.5 | 63.5 | 47.6 | 47.6 | 47.6 | 36.5 | 36.5 |
| 3 | 100 | 55.6 | 50.0 | 44.4 | 44.4 | 44.4 | 38.9 | 38.9 |

Example 8

Use of polysiloxanes of the current invention can be used in polishes for treating and finishing hard surfaces, in formulations for drying of automobiles and other hard surfaces after machine washing, as separate wrinkle reducers and quick drying agents after laundering textiles with detergent formulations, as quick drying wrinkle reducers in formulations containing surfactants for laundering textiles.

The evaluation of stain prevention was made in such a manner that 24.4 parts of the object of the current invention was diluted with 75.6 parts water. This solution was applied to terra cotta, marble and granite substrates and allowed to dry under ambient conditions. A variety of stain causing materials were applied to the treated substrates and allowed to stand for 4 hours. The substrates were washed with water, sponged, allowed to dry, and visually assessed for stain repellency. Treated substrates with no stains were given a score=0; 1=very light stain; 2=light stain; 3=moderate stain; 4=heavy stain; 5=stain penetrated within one hour. The result of the experimental evaluation of this hard surface stain prevention additive is shown in Table 6.

TABLE 6

Effect of Film Former on Stain Resistance

| SURFACE (Stain) | Untreated Stain Score | Emulsion-1A |
|---|---|---|
| TERRA COTTA: | | |
| Coffee | 4 | 1 |
| Ketchup | 4 | 3 |
| Olive Oil | 4 | 3 |
| GRANITE: | | |
| Coffee | 0 | 0 |
| Ketchup | 0 | 0 |
| Olive Oil | 3 | 0 |
| MARBLE: | | |
| Coffee | 4 | 1 |
| Ketchup | 3 | 3 |
| Olive Oil | 0 | 0 |
| TOTAL STAIN SCORE: | 22 | 11 |

Example 9

The use of a film forming adjuvant may be used to improve spray coverage and performance is by applying a spray mixture containing 0.75% glyphosate isopropyl amine salt and 1.0% of Emulsion 1 (Silicone of the present invention) at a spray volume of 100 L/ha, to barnyardgrass. The spray treatment containing the Silicone emulsion of the present invention is believed to improved weed control relative to herbicide alone.

The foregoing examples are merely illustrative of the invention, serving to illustrate only some of the features of the present invention. The appended claims are intended to claim the invention as broadly as it has been conceived and the examples herein presented are illustrative of selected embodiments from a manifold of all possible embodiments. Accordingly it is Applicant's (Applicants') intention that the appended claims are not to be limited by the choice of examples utilized to illustrate features of the present invention. As used in the claims, the word "comprises" and its grammatical variants also subtend and include phrases of varying and differing extent such as for example, but not limited thereto, "consisting essentially of" and "consisting of." Where necessary ranges have been supplied. It is to be expected that variations in these ranges will suggest themselves to a practitioner having ordinary skill in the art and where not already dedicated to the public, those variations should where possible be construed to be covered by the appended claims. It is also anticipated that advances in science and technology will make equivalents and substitutions possible that are not now contemplated by reason of the imprecision of language and these variations should also be construed where possible to be covered by the appended claims.

What is claimed is:

1. A composition comprising:
   a) colloidal silica core/silicone shell particles comprising (i) about 90 wt % to about 10 wt % cores of colloidal silica and (ii) about 10 wt % to about 90 wt % shells of a polyorganosiloxane having the formula $M_a D_b T_c Q_d$ with
   $M_a = (R^1)(R^2)(R^3)SiO_{2/2}$
   $D_b = (R^4)(R^5)SiO_{2/2}$,
   $T_c = (R^6)SiO_{3/2}$,
   $Q_d$ selected from the group consisting of (OH) $SiO_{3/2}$ or $SiO_{4/2}$ where $R^1$, $R^2$, $R^3$, $R^4$, $R^5$, and $R^6$ are each independently selected from the group consisting of OH, linear or branched monovalent hydrocarbon radicals of 1 to 30 carbons, monovalent arylalkyl, aryl cyclics hydrocarbon radicals where the ratios of M to D to T to Q are according to the following relationships:

$0 < (a/d) < 2$;

$0.1 < (b/d) < 10$;

$0 < (c/d) < 10$;

b) a polyalkyleneoxide modified trisiloxane having the formula:

$M^1_e D^1_f D^2_g M^2_h$ with
   $M^1_e = R^7 R^8 R^9 SiO_{1/2}$;
   $M^2_h = R^{10} R^{11} R^{12} SiO_{1/2}$;

$D^1_f = R^{13}R^{14}SiO_{2/2}$;
$D^2_g = R^{15}R^{16}SiO_{2/2}$;
where $R^7$, $R^{10}$ and $R^{15}$ are each independently selected from the group consisting of or 1 to 4 monovalent hydrocarbon radicals or $R^{17}$;
  subject to the following relationship that when g=0 then $R^7$ and $R^{10}$ are both $R^{17}$ when g is non-zero $R^7$ and $R^{10}$ are each independently selected from the group consisting of 1 to 4 monovalent hydrocarbon radicals;
  $R^{15}$ is $R^{17}$;
  $R^8$, $R^9$, $R^{11}$, $R^{12}$, $R^{13}$, $R^{14}$ and $R^{16}$ are independently selected from a group consisting of 1 to 4 monovalent hydrocarbon radicals;
where the subscripts e, f, g and h are zero or 1 subject to the following relationship:

$$e+f+g+h=3;$$

with the requirement that when g is 0, then $R^7$ or $R^{10}$ are $R^{17}$;
$R^{17}$ is an alkylenoxide group having the formula:

$$R^{18}O(C_2H_4O)_j(C_3H_6O)_k(C_4H_8O)_mR^{19}$$

where $R^{18}$ is a linear or branched hydrocarbon radical having from 2 to 6 carbons,
$R^{19}$ is selected from the group consisting of H, acetyl or a monovalent hydrocarbon radical of 1 to 6 carbon atoms and the subscripts j, k, and m are zero or a positive integer subject to the limitation that $4 < j+k+m \leq 20$;
  c) an emulsifier comprising an anionic surfactant derived selected from the group consisting of alkylarylsulfonates, alkylsulfonates, alkylsulfates and alkylethersufates, alkyl phosphate esters, alkylaryl phosphate esters, alcoholalkoxylate phosphate esters, and alkylarylalkoxylate phosphate esters and mixtures thereof; and
  d) the salt of an acidic polymerization catalyst.

2. The composition of claim 1 where $R^7$ is methyl.
3. The composition of claim 1 where $R^8$ is methyl.
4. The composition of claim 1 where $R^9$ is methyl.
5. The composition of claim 1 where $R^{10}$ is methyl.
6. The composition of claim 1 where $R^{11}$ is methyl.
7. The composition of claim 1 where $R^{12}$ is methyl.
8. The composition of claim 1 where the subscript k is 2 or 3.
9. The composition of claim 1 where $R^{18}$ has from 3 to 4 carbons.
10. The composition of claim 1 where $R^{19}$ is methyl or hydrogen.
11. The composition of claim 1 where $R^{17}$ is $CH_2CH_2CH_2\text{—}O\text{—}(CH_2CH_2\text{—}O)_8\text{—}H$ or $$CH_2CH(CH_3)CH_2\text{—}O\text{—}(CH_2\text{—}CH(CH_3)\text{—}O)_{12}\text{—}CH_3.$$

12. The composition of claim 1 where $R^7$, $R^8$, $R^9$, $R^{10}$, $R^{11}$, and $R^{12}$ is methyl, $R^{18}$ ranges from 3 to 4, $R^{19}$ is methyl or hydrogen
  and $R^{17}$ is $CH_2CH_2CH_2\text{—}O\text{—}(CH_2CH_2\text{—}O)_8\text{—}H$ or $CH_2CH(CH_3)CH_2\text{—}O\text{—}(CH_2\text{—}CH(CH_3)\text{—}O)_{12}\text{—}CH_3$.

13. A film comprising the composition of claim 12.
14. An emulsion comprising the composition of claim 1 where the composition of claim 1 is present in the discontinuous phase.
15. An emulsion comprising the composition of claim 1 where the composition of claim 1 is present in the continuous phase.
16. A film comprising the composition of claim 1.
17. A cosmetic composition comprising the composition of claim 1.
18. An agricultural composition comprising the composition of claim 1.
19. A home care composition comprising the composition of claim 1.

* * * * *